US006835841B2

(12) United States Patent
Deerberg et al.

(10) Patent No.: US 6,835,841 B2
(45) Date of Patent: Dec. 28, 2004

(54) ASYMMETRIC CATALYTIC HYDROGENATION PROCESS FOR PREPARATION OF CHIRAL CYCLIC β-AMINOESTERS

(75) Inventors: Joerg Deerberg, Bear, DE (US); Douglas D. McLeod, Kingston, NJ (US); Tai-Yuen Yue, Bear, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/660,345

(22) Filed: Sep. 11, 2003

(65) Prior Publication Data

US 2004/0082795 A1 Apr. 29, 2004

Related U.S. Application Data

(60) Provisional application No. 60/410,897, filed on Sep. 13, 2002.

(51) Int. Cl.$^7$ ...................... C07D 211/58; C07D 315/00; C07D 317/72; C07C 205/06
(52) U.S. Cl. ...................... 546/244; 549/342; 549/425; 560/156
(58) Field of Search ........................ 546/244; 549/342; 549/425; 560/156

(56) References Cited

FOREIGN PATENT DOCUMENTS

| EP | 062 840 | 3/1982 |
|---|---|---|
| EP | 250 179 | 6/1987 |
| WO | WO 00/43383 | 7/2000 |
| WO | WO 01/07433 | 2/2001 |
| WO | WO 01/70673 | 9/2001 |
| WO | WO 02/02525 | 1/2002 |
| WO | WO 02/24684 | 3/2002 |

OTHER PUBLICATIONS

Cimarelli, C.; Palmieri, G.; Bartoli, G.; "Diastereo and Enantioselective Entry to β–Amino Esters by Hydride Reduction of Homochiral β–Enamino Esters", Tetrahedron: Asymmetry, vol. 5, No. 8, pp. 1455–1458, 1994.
Xu, D.; Prasad, K.; Repič, O.; Blacklock, T. J.; "A practical synthesis of anantipure ethyl cis–2–amino–1– cyclohexanecarboxylate via asymmetric reductive amination methodology", Tetrahedron: Asymmetry, vol. 8, No.9, pp. 1445–1451, 1997.
Melillo, D. G.; Shinkai, I.; Liu, T., "A practical synthesis of (±)–Thienamycin", Tetrahedron Lett., vol. 21, 1980, pp. 2783–2786.
Melillo, D. G.; Cvetovich, R. J.;Ryan, K. M.; Sletzinger, M., "An Enantioselective Approach to (+)–Thienamycin from Dimethyl 1,3–Acetonedicarboxylate and (+)–α–Methylbenzylamine", J. Org. Chem. 1986, 51, pp. 1498–1504.

Haviari, G.; Céléier, J. P.; Lhommet, G.; Gardette, D.; Gramain, J. C.;" Asymmetric Synthesis with Chiral Hydrogenolysable Amines. Cyclic β–Enamino Ester Reduction A Diastereoselective Route to 2,3–Disubstituted Pyrrolidines", Tetrahedron Lett., vol. 33, pp. 4311–4312, 1992.
Haviari, G; Célérier, J. P.; Petit, H.; Lhommet, G.; "Asymmetric Synthesis with Chiral Hydrogenolysable Amines. A Short Synthesis of (–) Isoretronecanol", Tetrahedron Lett., vol. 34., No. 10, pp. 1599–1600, 1993.
Agami, C.; Kadouri–Puchot, C.; Le Guen, V.; Vaissermann, J., "Neuromediator Analogs: Synthesis of cis (2R,3S) and trans (2S,3S)–2,3–Piperidine Dicarboxylic Acids from (2S)–2–Phenylglycinol", Tetrahedron Lett., vol. 36, No. 10, pp. 1657–1660, 1995.
Cimarelli, C.; Palmieri, G.; "Stereoselective Reduction of Anantipure β–Anamino Esters by Hydride: A Convenient Synthesis of Both Enantiopure β–Amino Esters", J. Org. Chem. 1996, 61, pp. 5557–5563.
Hayashi, Y.; Rhode, J.J.; Corey, E.J.; "A Novel Chiral Super–Lewis Acidic Catalyst for Anantioselective Synthesis", J. Am. Chem. Soc. 1996, 118, pp. 5502–5503.
Agami, C.; Hamon, L.; Kadouri–Puchot, C.; Le Guen, V.; "Enantioselective Synthesis of Conformationally Restricted Analogs of NMDA: cis– and trans–Piperidine–2,3–dicarboxylic Acids and Methylated Derivatives", J. Org. Chem. 1996, 61, pp. 5736–5742.
Segat, F.; Lingibé, O.; Graffe, B.; Sacquet, M.C.; Lhommet, G.; "Asymmetric Synthesis with Chiral Hydrogenolysable Amines: A New Route to Enantiomerically Pure Amino Diols", Heterocycles, vol. 45, No. 8, pp. 1451–1455, 1997.
Blot, J.; Bardou, A.; Bellec, C.; Fargeau–Bellassoued, M. C.; Célérier, J. P.; Lhommet, G.; Gardette, D.; Gramain, J. C.; "Chiral Cyclic β–AMino Esters. Part II: Synthesis by Diastereoselective Reduction of Anamino Esters", Tetrahedron Lett. , vol. 38, No. 49, pp. 8511–8514, 1997.
Daley, V.; d'Angelo, J.; Cave, C.; Mahuteau.J.; Chiaroni, ,A.; Riche, C.; "A Novel Asymmetric Synthesis of 2,5–Dialkylpyrrolidines", Tetrahedron Letter, vol. 40, pp. 1657–1660, 1999.
David, O et al., "Enamino Ester Reduction: A Short Enantioselective Route to Pyrrolizidine and Indolizidine Alkaloids. Synthesis of (+)–Laburnine, (+)–Tashiromine, and (–)–Isoretronecanol", J. Org. Chem. 1999, 64, 3122–3131.
Zhong, H. M.; Cohen, J. H.; Abdel–Magid, A. F.; Kenney, B. D.; Maryanoff, C. A.; Shah, R. D.; Villani, F. J., Jr.; Zhang, F.; Zhang, X.; "An efficient stereoselective synthesis of methyl (S)–3–amino–3–(3–pyridyl)propanoate", Tetrahedron Lett. 1999,40, 7721–7725.

(List continued on next page.)

Primary Examiner—Taofiq Solola
(74) Attorney, Agent, or Firm—Jing S. Belfield

(57) ABSTRACT

A novel process for the asymmetric synthesis of substituted cyclic β-amino-carboxylates of the type shown in the specification from appropriate β-enamino-ester starting materials is described. These compounds are useful as intermediates for MMP and TACE inhibitors.

25 Claims, No Drawings

OTHER PUBLICATIONS

Mechelke, M. F.; Meyers, A. I.; "An efficient, asymmetric synthesis of (+)-euphoccoccine", Tetrahedron Lett. 2000, 41, 4339–4342.

David, O.; Bellec, C.; Fargeau–Bellassoued; Lhommet, G.; "Diastereoselective reduction of chiral enaminolactones: A short and convenient route to anantiopure(+)–tashiromine", Heterocycles, vol. 55, No. 9, 1689–1701, 2001.

Wang, G. T., et al; "Design, Synthesis, and Structural Analysis of Influenza Neuraminidase Inhibitors Containing Pyrrolidine Cores", J. Med. Chem. 2001, 44, 1192–1201.

ASYMMETRIC CATALYTIC HYDROGENATION PROCESS FOR PREPARATION OF CHIRAL CYCLIC β-AMINOESTERS

CROSS-REFERENCE TO RELATED APPLICATIONS

The present application claims the priority benefit of U.S. Provisional Application No. 60/410,897, filed Sep. 13, 2002, which is expressly incorporated fully herein by reference.

FIELD OF THE INVENTION

The present invention relates generally to processes for the synthesis of chiral cyclic β-aminoesters, such compounds being useful as intermediates for matrix metalloproteinases (MMP) and TNF-α converting enzyme (TACE) inhibitors.

BACKGROUND OF THE INVENTION

The present invention relates to processes for the preparation of chiral cyclic β-aminoesters, which are useful as intermediates in the preparation of MMP and TACE inhibitors. In particular, the present invention provides a process for the preparation of 4-amino-tetrahydro-4H-pyran-3-carboxylate. The general processes disclosed in the art (e.g., C. Cimarelli et al. *Tetrahedron-Asymmetry* 1994, 5, 1455) provide 4-amino-tetrahydro-4H-pyran-3-carboxylate in low and inconsistent yields of the desired stereoisomer. In contrast to the previously known processes, the present invention provides more practical and economical methodology for the preparation of (3R,4R)-4-aminotetrahydro-4H-pyran-3-carboxylate in relatively high yield and isomeric purity.

The present invention provides access to such β-aminoesters with increased selectivity in the reduction step, resulting in higher yields and isomeric purity of products. In contrast to protocols known in the art using borohydrides as reducing agents (D. Xu et al. *Tetrahedron-Asymmetry* 1997, 8, 1445), throughput has been increased significantly due to low process volumes. Chiral cyclic β-aminoester products can now be isolated by salt formation directly from the filtered reaction mass, thereby obviating the need for aqueous work-up procedures.

SUMMARY OF THE INVENTION

Accordingly, the present invention provides novel processes for making chiral cyclic β-aminoesters.

The present invention provides novel hydrobromide salts of the chiral cyclic β-aminoesters.

These and other objects, which will become apparent during the following detailed description, have been achieved by the inventors' discovery that compounds of formula II can be formed from compounds of formula I (* denotes a chiral center).

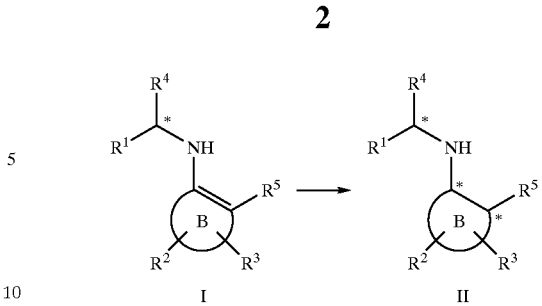

DETAILED DESCRIPTION OF THE INVENTION

In an embodiment, the present invention provides, inter alia, a novel process of forming a compound of formula II, comprising:

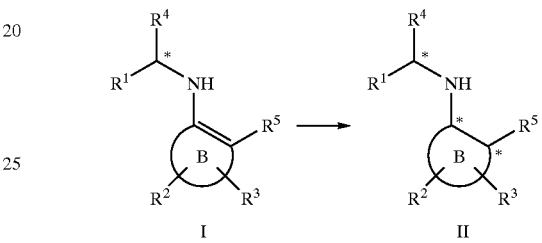

(a) contacting a compound of formula I with substoichiometric amounts of a platinum catalyst in the presence of a solvent under hydrogen pressure and superstoichiometric amounts of an acid; wherein:

the platinum catalyst is platinum on charcoal (Pt/C) or Adam's catalyst (platinum(IV)-dioxide, $PtO_2$);

the solvent is a protic solvent or a mixture of protic and aprotic solvents;

ring B is a 4–7 membered non-aromatic carbocyclic or heterocyclic ring consisting of: carbon atoms, 0–3 carbonyl groups, 0–3 double bonds, and 0–2 ring heteroatoms selected from O, N, $NR^6$, and $S(O)_p$, provided that ring B contains other than a S—S, O—O, or S—O bond;

$R^1$ is Q, —$C_{1-6}$ alkylene-Q, —$C_{2-6}$ alkenylene-Q, or —$C_{2-6}$ alkynylene-Q;

$R^2$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_r$ $NR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)$ $NR^aR^{a1}$, —$(CR^aR^{a1})_rC(O)NR^a(CR^aR^{a1})_s$-Q, —$(CR^aR^{a1})_rS$ $(O)_p(CR^aR^{a1})_s$-Q, or —$(CR^aR^{a1})_rSO_2NR^a(CR^aR^{a1})_s$-Q;

Q is, independently at each occurrence, H, a $C_{3-6}$ carbocycle substituted with 0–3 $R^d$, or a 5–10 membered heterocycle consisting of: carbon atoms and 1–4 heteroatoms selected from the group consisting of N, O, and $S(O)_p$, and substituted with 0–3 $R^d$;

$R^3$ is H, Cl, F, $C_{1-6}$ alkyl, $C_{2-6}$ alkenyl, $C_{2-6}$ alkynyl, —$(CH)_r$-phenyl substituted with 0–3 $R^d$, or —$(CH)_r$-5–6 membered heterocycle consisting of: carbon atoms and 1–4 heteroatoms selected from the group consisting of N, O, and $S(O)_p$, and substituted with 0–3 $R^d$;

alternatively, when $R^2$ and $R^3$ are attached to the same carbon atom, they form a 3–8 membered carbocyclic or heterocyclic spiro ring C substituted with 0–2 $R^c$ and consisting of carbon atoms, 0–4 heteroatoms selected from O, N, and $S(O)_p$, and 0–2 double bonds, provided that ring C contains other than a S—S, O—O, or S—O bond;

alternatively, when $R^2$ and $R^3$ are attached to adjacent carbon atoms, together with the carbon atoms to which they are attached they form a 5–7 membered carbocyclic or heterocyclic ring D substituted with 0–2 $R^c$ and consisting of carbon atoms, 0–2 heteroatoms selected from the group consisting of N, O, and $S(O)_p$, and 0–3 double bonds;

$R^4$ is H, $C_{1-6}$ alkyl substituted with 0–1 $R^b$, $C_{2-6}$ alkenyl substituted with 0–1 $R^b$, or $C_{2-6}$ alkynyl substituted with 0–1 $R^b$;

$R^5$ is —$CH_2OR^a$ or —$C(O)OR^a$;

$R^6$ is Q, —$C_{1-6}$ alkylene-Q, —$C_{2-6}$ alkenylene-Q, —$C_{2-6}$ alkynylene-Q, —$(CR^aR^{a1})_rC(O)(CR^aR^{a1})_s$-Q, —$(CR^aR^{a1})_r$ $C(O)$—$C_{2-6}$ alkenylene-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a$ $(CR^aR^{a1})_s$-Q, —$(CR^aR^{a1})_rS(O)_p(CR^aR^{a1})_s$-Q, or —$(CR^aR^{a1})_rSO_2NR^a(CR^aR^{a1})_s$-Q;

$R^a$ is, independently at each occurrence, H, $C_{1-6}$ alkyl, phenyl, or benzyl;

$R^{a1}$ is, independently at each occurrence, H or $C_{1-6}$ alkyl;

$R^{a2}$ is, independently at each occurrence, $C_{1-6}$ alkyl, phenyl, or benzyl;

$R^b$ is, independently at each occurrence, $C_{1-6}$ alkyl substituted with 0–1 $R^c$, —$OR^a$, —$SR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a2}$, —$NR^aS(O)_2NR^aR^{a1}$, —$OS(O)_2NR^aR^{a1}$, —$S(O)_pR^{a2}$, $CF_3$, —$CF_2CF_3$, —$CHF_2$, —$CH_2F$, or phenyl;

$R^c$ is, independently at each occurrence, H, $C_{1-4}$ alkyl, —$OR^a$, Cl, F, Br, I, =O, $CF_3$, CN, $NO_2$, —$C(O)R^a$, —$C(O)OR^a$, —$C(O)NR^aR^a$, or —$S(O)_pR^a$;

$R^d$ is, independently at each occurrence, $C_{1-6}$ alkyl, —$OR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)$ $NR^aR^{a1}$, —$OC(O)NR^aR^{a1}$, —$NR^aC(O)OR^a$, —$S(O)_2$ $NR^aR^{a1}$, —$NR^aS(O)_2R^{a2}$, —$NR^aS(O)_2NR^aR^{a1}$, —$OS(O)_2$ $NR^aR^{a1}$, —$S(O)_pR^{a2}$, $CF_3$, —$CF_2CF_3$, $C_{3-10}$ carbocycle, or a 5–6 membered heterocycle consisting of: carbon atoms and 1–4 heteroatoms selected from the group consisting of N, O, and $S(O)_p$;

p, at each occurrence, is selected from 0, 1, and 2;

r, at each occurrence, is selected from 0, 1, 2, 3, and 4; and s, at each occurrence, is selected from 0, 1, 2, 3, and 4.

In another embodiment, the present invention provides a novel process of forming a compound of formula II, wherein:

ring B is:

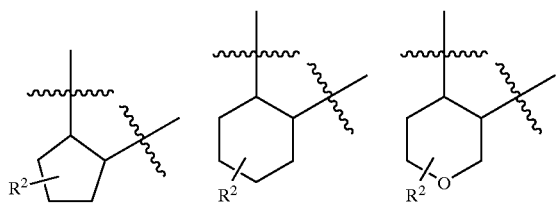

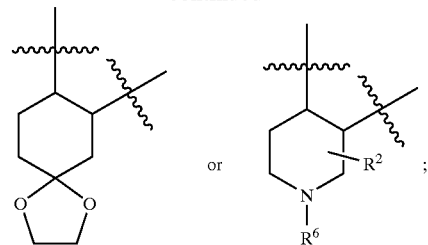

$R^1$ is phenyl substituted with 0–3 $R^d$;

$R^2$ is Q, —$C_{1-6}$ alkylene-Q, —$C_{2-4}$ alkenylene-Q, —$C_{2-4}$ alkynylene-Q, —$C(O)(CR^aR^{a1})_s$-Q, —$C(O)O(CR^aR^{a1})_s$-Q, —$C(O)NR^aR^{a1}$, —$C(O)NR^a(CR^aR^{a1})_s$-Q, —$S(O)_p$ $(CR^aR^{a1})_s$-Q, or —$SO_2NR^a(CR^aR^{a1})_s$-Q;

Q is, independently at each occurrence, H, cyclopropyl, cyclobutyl, cyclopentyl, cyclohexyl, tetrahydro-2H-pyran-4-yl, or phenyl substituted with 0–2 $R^d$;

$R^4$ is $C_{1-4}$ alkyl;

$R^5$ is —$CH_2OR^a$ or —$C(O)OR^a$;

$R^6$ is Q, —$C_{1-6}$ alkylene-Q, —$C_{2-4}$ alkenylene-Q, —$C_{2-4}$ alkynylene-Q, —$C(O)(CR^aR^{a1})_s$-Q, —$C(O)O(CR^aR^{a1})_s$-Q, —$C(O)NR^aR^{a1}$, —$C(O)NR^a(CR^aR^{a1})_s$-Q, —$S(O)_p$ $(CR^aR^{a1})_s$-Q, or —$SO_2NR^a(CR^aR^{a1})_s$-Q; and $R^d$ is, independently at each occurrence, $C_{1-6}$ alkyl, —$OR^a$, Cl, F, Br, =O, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a2}$, —$S(O)_pR^{a2}$, $CF_3$ or phenyl.

In another embodiment, the present invention provides a novel process of forming a compound of formula II, wherein:

ring B is:

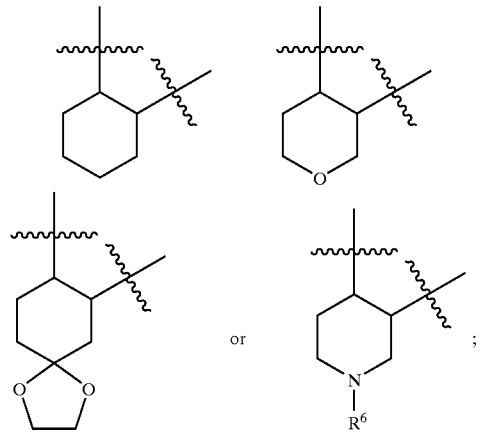

$R^1$ is phenyl;

$R^4$ is $C_{1-4}$ alkyl;

$R^5$ is —$C(O)OR^a$;

$R^6$ is H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, or tetrahydro-2H-pyran-4-yl; and $R^a$ is $C_{1-4}$ alkyl.

In another embodiment, the present invention provides a novel process further comprising:

(b) contacting the product from (a) with a hydrogen bromide solution in an acid to yield compound III;

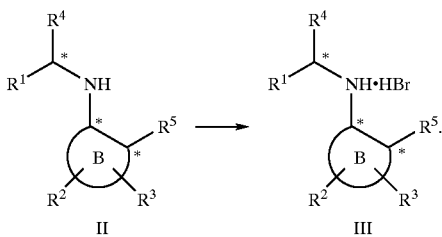

In another embodiment, the present invention provides a novel process further comprising:

(c) contacting the product from (b) with palladium on charcoal catalyst (Pd/C) in the presence of a solvent under hydrogen pressure to yield compound IV; wherein the solvent is a protic solvent or a mixture of protic and aprotic solvents;

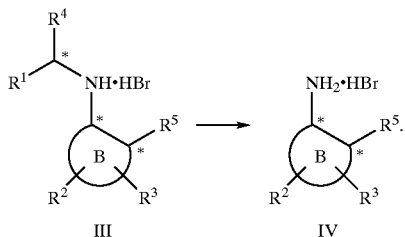

In another embodiment, the present invention provides a novel process, wherein in (a):

the protic solvent is methanol, ethanol, propanol, 2-butanol, water, ethylene glycol, propylene glycol, or butylene glycol; and the aprotic solvent is tetrahydrofuran, dibutyl ether, 1,2-dimethoxyethane, dimethoxymethane, or diethoxymethane.

In another embodiment, the present invention provides a novel process, wherein in (a):

the protic solvent is selected from: methanol, ethanol, propanol, and 2-butanol; and the aprotic solvent is selected from: tetrahydrofuran and dimethoxymethane.

In another embodiment, the present invention provides a novel process, wherein in (a):

the protic solvent is methanol; and the aprotic solvent is tetrahydrofuran.

In another embodiment, the present invention provides a novel process, wherein in (a):

the hydrogen pressure is 10 to 400 psig.

In another embodiment, the present invention provides a novel process, wherein in (a):

the hydrogen pressure is 100 to 300 psig.

In another embodiment, the present invention provides a novel process, wherein in (a):

the hydrogen pressure is 250 psig.

In another embodiment, the present invention provides a novel process, wherein in (a):

the acid is selected from: formic acid, acetic acid, chloroacetic acid, dichloroacetic acid, trichloroacetic acid, trifluoroacetic acid, propionic acid, isobutyric acid, hydrochloric acid, and sulfuric acid.

In another embodiment, the present invention provides a novel process, wherein in (a):

the acid is acetic acid.

In another embodiment, the present invention provides a novel process, wherein in (b):

the acid is acetic acid or formic acid.

In another embodiment, the present invention provides a novel process, wherein in (b):

the acid is acetic acid.

In another embodiment, the present invention provides a novel process, wherein in (c):

the protic solvent is selected from: methanol, ethanol, propanol, 2-butanol, water, ethylene glycol, propylene glycol, and butylene glycol; and the aprotic solvent is selected from: tetrahydrofuran, dibutyl ether, 1,2-dimethoxyethane, dimethoxymethane, and diethoxymethane.

In another embodiment, the present invention provides a novel process, wherein in (c):

the protic solvent is selected from: methanol, ethanol, propanol, and 2-butanol; and the aprotic solvent is selected from: tetrahydrofuran and dimethoxymethane.

In another embodiment, the present invention provides a novel process, wherein in (c):

the protic solvent is methanol; and the aprotic solvent is tetrahydrofuran.

In another embodiment, the present invention provides a novel process, wherein in (c):

the hydrogen pressure is 20 to 300 psig.

In another embodiment, the present invention provides a novel process, wherein in (c):

the hydrogen pressure is 50 to 150 psig.

In another embodiment, the present invention provides a novel process, wherein in (c):

the hydrogen pressure is 100 psig.

In another embodiment, the present invention provides the diastereomeric ratio of the product of (a), Compound of formula II, at least 60%.

In another embodiment, the present invention provides the diastereomeric ratio of the product of (a), Compound of formula II, at least 80%.

In another embodiment, the present invention provides the diastereomeric ratio of the product of (c), Compound of formula IV, at least 60%; and, the enantiomeric ratio of the product of (c), Compound of formula IV, at least 60%.

In another embodiment, the present invention provides the diastereomeric ratio of the product of (c), Compound of formula IV, at least 80%; and, the enantiomeric ratio of the product of (c), Compound of formula IV, at least 80%.

In another embodiment, the present invention provides a novel compound of formula III or IV:

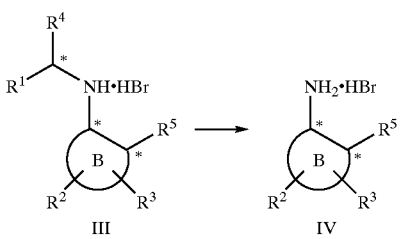

wherein:

ring B is a 4–7 membered non-aromatic carbocyclic or heterocyclic ring consisting of: carbon atoms, 0–3 carbonyl groups, 0–3 double bonds, and 0–2 ring heteroatoms selected from O, N, $NR^6$, and $S(O)_p$, provided that ring B contains other than a S—S, O—O, or S—O bond;

$R^1$ is Q, —$C_{1-6}$ alkylene-Q, —$C_{2-6}$ alkenylene-Q, or —$C_{2-6}$ alkynylene-Q;

$R^2$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_r NR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O) NR^aR^{a1}$, —$(CR^aR^{a1})_rC(O)NR^a(CR^aR^{a1})_s$-Q, —$(CR^aR^{a1})_rS(O)_p(CR^aR^{a1})_s$-Q, or —$(CR^aR^{a1})_rSO_2NR^a(CR^aR^{a1})_s$-Q;

Q is, independently at each occurrence, H, a $C_{3-6}$ carbocycle substituted with 0–3 $R^d$, or a 5–10 membered heterocycle consisting of: carbon atoms and 1–4 heteroatoms selected from the group consisting of N, O, and $S(O)_p$, and substituted with 0–3 $R^d$;

$R^3$ is H, Cl, F, $C_{1-6}$ alkyl, $C_{2-6}$ alkenyl, $C_{2-6}$ alkynyl, —$(CH)_r$-phenyl substituted with 0–3 $R^d$, or —$(CH)_r$-5–6 membered heterocycle consisting of: carbon atoms and 1–4 heteroatoms selected from the group consisting of N, O, and $S(O)_p$, and substituted with 0–3 $R^d$;

alternatively, when $R^2$ and $R^3$ are attached to the same carbon atom, they form a 3–8 membered carbocyclic or heterocyclic spiro ring C substituted with 0–2 $R^c$ and consisting of carbon atoms, 0–4 heteroatoms selected from O, N, and $S(O)_p$, and 0–2 double bonds, provided that ring C contains other than a S—S, O—O, or S—O bond;

alternatively, when $R^2$ and $R^3$ are attached to adjacent carbon atoms, together with the carbon atoms to which they are attached they form a 5–7 membered carbocyclic or heterocyclic ring D substituted with 0–2 $R^c$ and consisting of carbon atoms, 0–2 heteroatoms selected from the group consisting of N, O, and $S(O)_p$, and 0–3 double bonds;

$R^4$ is H, $C_{1-6}$ alkyl substituted with 0–1 $R^b$, $C_{2-6}$ alkenyl substituted with 0–1 $R^b$, or $C_{2-6}$ alkynyl substituted with 0–1 $R^b$;

$R^5$ is —$CH_2OR^a$ or —$C(O)OR^a$;

$R^6$ is Q, —$C_{1-6}$ alkylene-Q, —$C_{2-6}$ alkenylene-Q, —$C_{2-6}$ alkynylene-Q, —$(CR^aR^{a1})_rC(O)(CR^aR^{a1})_s$-Q, —$(CR^aR^{a1})_r C(O)$—$C_{2-6}$ alkenylene-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a (CR^aR^{a1})_s$-Q, —$(CR^aR^{a1})_rS(O)_p(CR^aR^{a1})_s$-Q, or —$(CR^aR^{a1})_rSO_2NR^a(CR^aR^{a1})_s$-Q;

$R^a$ is, independently at each occurrence, H, $C_{1-6}$ alkyl, phenyl, or benzyl;

$R^{a1}$ is, independently at each occurrence, H or $C_{1-6}$ alkyl;

$R^{a2}$ is, independently at each occurrence, $C_{1-6}$ alkyl, phenyl, or benzyl;

$R^b$ is, independently at each occurrence, $C_{1-6}$ alkyl substituted with 0–1 $R^c$, —$OR^a$, —$SR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a2}$, —$NR^aS(O)_2NR^aR^{a1}$, —$OS(O)_2NR^aR^{a1}$, —$S(O)_pR^{a2}$, $CF_3$, —$CF_2CF_3$, —$CHF_2$, —$CH_2F$, or phenyl;

$R^c$ is, independently at each occurrence, H, $C_{1-4}$ alkyl, —$OR^a$, Cl, F, Br, I, =O, $CF_3$, CN, $NO_2$, —$C(O)R^a$, —$C(O)OR^a$, —$C(O)NR^aR^a$, or —$S(O)_pR^a$;

$R^d$ is, independently at each occurrence, $C_{1-6}$ alkyl, —$OR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O) NR^aR^{a1}$, —$OC(O)NR^aR^{a1}$, —$NR^aC(O)OR^a$, —$S(O)_2 NR^aR^{a1}$, —$NR^aS(O)_2R^{a2}$, —$NR^aS(O)_2NR^aR^{a1}$, —$OS(O)_2 NR^aR^{a1}$, —$S(O)_pR^{a2}$, $CF_3$, —$CF_2CF_3$, $C_{3-10}$ carbocycle, or a 5–6 membered heterocycle consisting of: carbon atoms and 1–4 heteroatoms selected from the group consisting of N, O, and $S(O)_p$;

p, at each occurrence, is selected from 0, 1, and 2;

r, at each occurrence, is selected from 0, 1, 2, 3, and 4; and s, at each occurrence, is selected from 0, 1, 2, 3, and 4;

provided that ring B is other than cyclohexane.

In another embodiment, the present invention provides a compound of formula III or IV, wherein:

ring B is selected from:

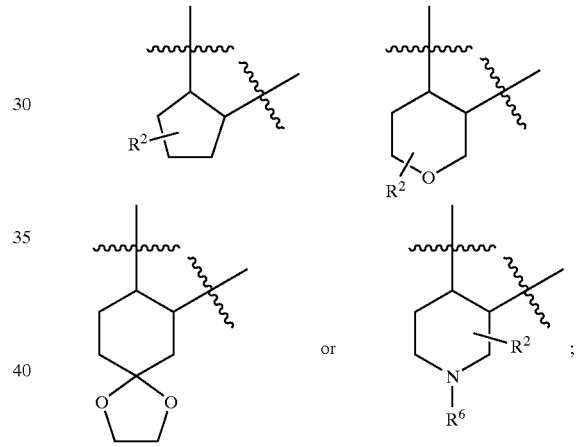

$R^1$ is phenyl substituted with 0–3 $R^d$;

$R^2$ is Q, —$C_{1-6}$ alkylene-Q, —$C_{2-4}$ alkenylene-Q, —$C_{2-4}$ alkynylene-Q, —$C(O)(CR^aR^{a1})_s$-Q, —$C(O)O(CR^aR^{a1})_s$-Q, —$C(O)NR^aR^{a1}$, —$C(O)NR^a(CR^aR^{a1})_s$-Q, —$S(O)_p (CR^aR^{a1})_s$-Q, or —$SO_2NR^a(CR^aR^{a1})_s$-Q;

Q is, independently at each occurrence, H, cyclopropyl, cyclobutyl, cyclopentyl, cyclohexyl, tetrahydro-2H-pyran-4-yl, or phenyl substituted with 0–2 $R^d$;

$R^4$ is $C_{1-4}$ alkyl;

$R^5$ is —$CH_2OR^a$ or —$C(O)OR^a$;

$R^6$ is Q, —$C_{1-6}$ alkylene-Q, —$C_{2-4}$ alkenylene-Q, —$C_{2-4}$ alkynylene-Q, —$C(O)(CR^aR^{a1})_s$-Q, —$C(O)O(CR^aR^{a1})_s$-Q, —$C(O)NR^aR^{a1}$, —$C(O)NR^a(CR^aR^{a1})_s$-Q, —$S(O)_p (CR^aR^{a1})_s$-Q, or —$SO_2NR^a(CR^aR^{a1})_s$-Q; and $R^d$ is, independently at each occurrence, $C_{1-6}$ alkyl, —$OR^a$, Cl, F, Br, =O, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a2}$, —$S(O)_p R^{a2}$, $CF_3$ or phenyl.

In another embodiment, the present invention provides a novel compound of formula II or IV; wherein:

ring B is:

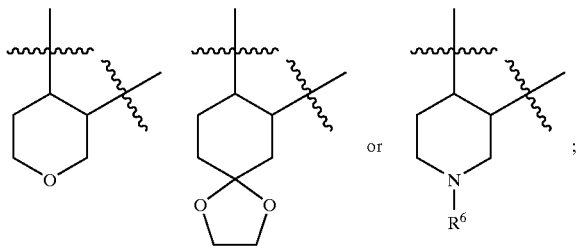

R¹ is phenyl;
R⁴ is C$_{1-4}$ alkyl;
R⁵ is —C(O)OR$^a$;
R⁶ is H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, or tetrahydro-2H-pyran-4-yl; and
R$^a$ is C$_{1-4}$ alkyl.

Definitions

The present invention can be practiced on multigram scale, kilogram scale, multikilogram scale, or industrial scale. Multigram scale, as used herein, is preferable in the scale wherein at least one starting material is present in 10 grams or more, more preferable at least 50 grams or more, even more preferably at least 100 grams or more. Multikilogram scale, as used herein, is intended to mean the scale wherein more than one kilo of at least one starting material is used. Industrial scale as used herein is intended to mean a scale which is other than a laboratory sale and which is sufficient to supply product sufficient for either clinical tests or distribution to consumers.

As used herein, the following terms and expressions have the indicated meanings. It will be appreciated that the compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, and racemic forms and all geometric isomeric forms of a structure are intended, unless the specific stereochemistry or isomer form is specifically indicated.

As used herein, equivalents are intended to mean molar equivalents unless otherwise specified.

As used herein, psig (pounds per square inch, gauge) is intended to mean pounds per square inch above ambient atmospheric pressure. Therein, one pound per square inch equals 0.070 kilograms per square centimeters of pressure.

The reactions of the synthetic methods claimed herein are carried out in suitable solvents which may be readily selected by one of skill in the art of organic synthesis, the suitable solvents generally being any solvent which is substantially non-reactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable protic solvents may include, by way of example and without limitation, methanol, ethanol, n-propanol, isopropanol, butanol, particularly 2-butanol, water, ethylene glycol, propylene glycol, butylene glycol and a mixture thereof.

Suitable aprotic solvents may include, by way of example and without limitation, aliphatic hydrocarbons, ether solvents, tetrahydrofuran (THF), dimethylformamide (DMF), dimethyl sulfoxide (DMSO), 1,2-dimethoxyethane, diethoxymethane, dimethoxymethane, dimethylacetamide (DMAC), benzene, toluene, 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, hexamethylphosphortriamide, or a mixture thereof.

As used herein, an alcohol solvent is a hydroxy-substituted compound that is liquid at the desired temperature (e.g., room temperature). Examples of alcohols include, but are not limited to, methyl alcohol, ethyl alcohol, n-propanol, and i-propanol.

Suitable esters may include, by way of example and without limitation, methyl acetate, ethyl acetate, propyl acetate, isopropyl acetate, butyl acetate, isobutyl acetate, amyl acetate, isoamyl acetate, benzyl acetate, phenyl acetate, methyl propionate, ethyl propionate, propyl propionate, isopropyl propionate, butyl propionate, isobutyl propionate, amyl propionate, isoamyl propionate, benzyl propionate, phenyl propionate, methyl butyrate, ethyl butyrate, propyl butyrate, isopropyl butyrate, butyl butyrate, isobutyl butyrate, amyl butyrate, isoamyl butyrate, benzyl butyrate, and phenyl butyrate.

As used herein, the term "amino protecting group" (or "N-protected") refers to any group known in the art of organic synthesis for the protection of amine groups. As used herein, the term "amino protecting group reagent" refers to any reagent known in the art of organic synthesis for the protection of amine groups that may be reacted with an amine to provide an amine protected with an amine-protecting group. Such amine protecting groups include those listed in Greene and Wuts, "*Protective Groups in Organic Synthesis*" John Wiley & Sons, New York, 1991 and "*The Peptides: Analysis, Synthesis, Biology*", 1981, Vol. 3, Academic Press, New York, the disclosure of which is hereby incorporated by reference. Examples of amine protecting groups include, but are not limited to, the following: 1) acyl types such as formyl, trifluoroacetyl (TFA), phthalyl, and p-toluenesulfonyl; 2) aromatic carbamate types such as benzyloxycarbonyl (cbz) and substituted benzyloxycarbonyls, 2-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10,10-tetrahydrothioxanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl;

p-nitrobenzyloxycarbonyl; 2-(p-toluenesulfonyl) ethyloxycarbonyl; m-chloro-p-acyloxybenzyloxycarbonyl; 5-benzyisoxazolylmethyloxycrbonyl; p-(dihydroxyboryl) benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; and methanesulfonamide.

Preferably, the molecular weight of compounds of the present invention is less than about 500, 550, 600, 650, 700, 750, 800, 850, 900, 950, or 1000 grams per mole. More preferably, the molecular weight is less than about 950 grams per mole. Even more preferably, the molecular weight is less than about 850 grams per mole. Still more preferably, the molecular weight is less than about 750 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4H-carbazolyl, carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2, 3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, imidazo[1,2-a]pyridinyl, imidazo[1,5-a]pyridinyl, and pyrazolo[1,5-a]pyridinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Stable compound" and "stable structure" are meant to indicate a compound that is sufficiently robust to survive isolation to a useful degree of purity from a reaction mixture, and formulation into an efficacious therapeutic agent.

Synthesis

By way of example and without limitation, the present invention may be further understood by the following schemes and descriptions. Scheme 1 exemplifies how a desired end product can be formed using the presently claimed processes and intermediates.

Scheme 1

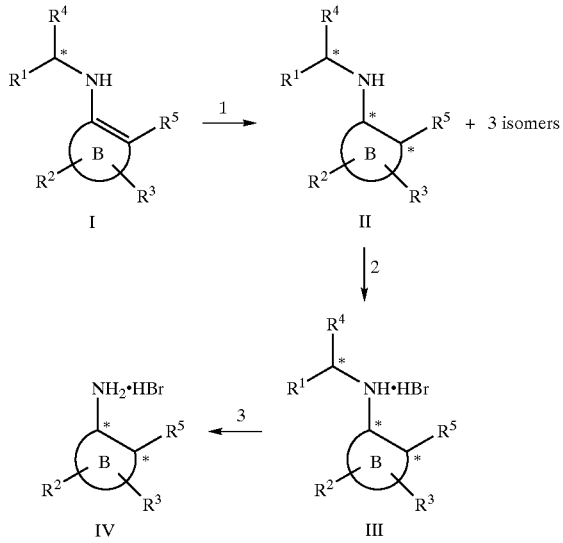

Starting Material: chiral cyclic β-enaminoesters can be obtained commercially or prepared by methods known to those of ordinary skill in the art.

Reaction 1: Reaction 1 generally involves catalytic hydrogenation of chiral cyclic β-enaminoesters by contacting Compound I with sub-stoichiometric amounts of a platinum catalyst in the presence of a solvent under hydrogen pressure and super-stoichiometric amounts of an acid. Preferably, the platinum catalyst is platinum on charcoal (Pt/C) or Adam's catalyst (platinum(IV)-dioxide, $PtO_2$). Preferably, the solvent is a protic solvent or a mixture of protic and aprotic solvents. The catalyst is preferably removed by filtration, rinsing with a protic solvent or a mixture of a protic and aprotic solvent. The filtrate is preferably evaporated to a low volume and co-evaporated with an ester solvent.

Preferably, the protic solvent is methanol, ethanol, propanol, 2-butanol, water, ethylene glycol, propylene glycol, butylene glycol, or a mixture thereof. More preferably, the protic solvent is methanol, ethanol, propanol, or 2-butanol. Even more preferably, the protic solvent is methanol.

Preferably, the aprotic solvent used in the mixture of protic and aprotic solvents is an ether solvent, such as tetrahydrofuran (THF), dibutyl ether, 1,2-dimethoxyethane (DME), dimethoxymethane or diethoxymethane. More preferably, the aprotic ether solvent is THF or 1,2-dimethoxyethane. Even more preferably, the aprotic ether solvent is THF.

Preferred acids used in conjunction with the platinum catalyst (i.e., Pt/C or $PtO_2$) include, but are not limited to, formic acid, acetic acid, chloroacetic acid, dichloroacetic acid, trichloroacetic acid, trifluoroacetic acid, propionic acid, isobutyric acid, hydrochloric acid, and sulfuric acid. A more preferred acid is acetic acid.

Preferred esters used in co-evaporation with compound II include, but are not limited to, methyl acetate, ethyl acetate, isopropyl acetate, n-butyl acetate, tert-butyl acetate and isobutyl acetate. A preferred ester is isopropyl acetate.

Preferably, the hydrogen pressure is 10 to 400 psig. More preferably, the hydrogen pressure is 100 to 300 psig. Even more preferably, the hydrogen pressure is 250 psig (17.5 bar).

Compound II resulting from Reaction 1 has three stereocenters. Preferably, the diastereoselectivity (i.e., diastereomeric ratio, d.r.) for the newly formed chiral centers with respect to the existing stereocenter is equal to or greater than 60% d.r. More preferably the diastereomeric ratio is equal to or greater than 80% d.r. Even more preferably the diastereomeric ratio is equal to or greater than 85% d.r.

Reaction 2: Optionally, isomeric purity of chiral cyclic β-aminoesters can be further enhanced by crystallization of a suitable salt (compound III) of compound II by methods known to those of skill in the art of organic synthesis. For example, compound II can be treated with a hydrogen bromide solution in an acid to yield compound III.

Preferred solvents used for the hydrogen bromide solution include, but are not limited to, acetic acid and formic acid. A more preferred acid is acetic acid.

Reaction 3: Reaction 3 involves cleavage of the auxiliary by methods known to those of skill in the art of organic synthesis. For example, this can be achieved by contacting Compound III with palladium on charcoal catalyst (Pd/C) in the presence of a solvent under hydrogen pressure. Preferably, the solvent is a protic solvent or a mixture of protic and aprotic solvents. The catalyst is preferably removed by filtration. The filtrate is typically evaporated to a low volume and co-evaporated with an anti-solvent, such as an ester solvent.

Preferably, the protic solvent is methanol, ethanol, propanol, 2-butanol, water, ethylene glycol, propylene glycol, butylene glycol, or a mixture thereof. More preferably, the protic solvent is methanol, ethanol, or isopropanol. Even more preferably, the protic solvent is methanol.

Preferably, the aprotic solvent used in the mixture of protic and aprotic solvents is an ether solvent, such as tetrahydrofuran (THF), dibutyl ether, 1,2-dimethoxyethane (DME), dimethoxymethane or diethoxymethane. More preferably, the aprotic ether solvent is THF or 1,2-dimethoxyethane. Even more preferably, the aprotic ether solvent is THF.

Preferred esters used in co-evaporation with compound II include, but are not limited to, methyl acetate, ethyl acetate, isopropyl acetate, n-butyl acetate, tert-butyl acetate and isobutyl acetate. A preferred ester is isopropyl acetate.

Preferably, the hydrogen pressure is 20 to 300 psig. More preferably, the hydrogen pressure is 50 to 150 psig. Even more preferably, the hydrogen pressure is 100 psig.

Compound IV resulting from Reaction 3 has two stereocenters. Preferably, the diastereomeric ratio between the two chiral centers is equal to or greater than 60% d.r. More preferably the diastereomeric ratio is equal to or greater than 80% d.r. Even more preferably the diastereomeric ratio is equal to or greater than 85% d.r.

Preferably, the enantioselectivity (i.e., enantiomeric ratio e.r.) is equal to or greater than 60% e.r. More preferably the enantiomeric ratio is equal to or greater than 80% e.r. Even more preferably the enantiomeric ratio is equal to or greater than 85% e.r.

Preferably, the temperature range for Reactions 1–3 is 5 to 100° C. More preferably the temperature range is 10 to 50° C. Even more preferably the temperature range is 20 to 45° C.

Other features of the invention will become apparent in the course of the following descriptions of examplary embodiments which are given for illustration of the invention and are not intended to be limiting thereof.

EXAMPLES

Abbreviations used in the Examples are defined as follows: "1 x" for once, "2 x" for twice, "3 x" for thrice, "° C." for degrees Celsius, "eq" for equivalent or equivalents, "g" for gram or grams, "mg" for milligram or milligrams, "mL" for milliliter or milliliters, "$\mu$L" for microliter or microliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

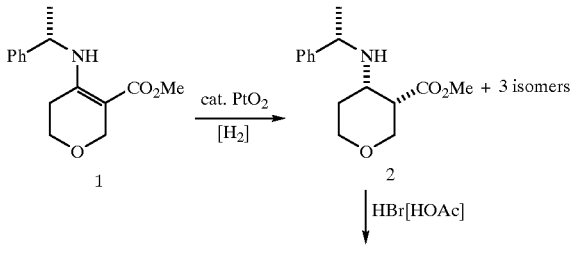

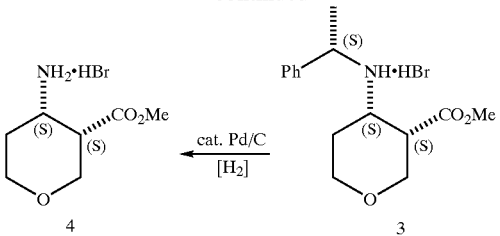

Compound 3: Methyl (1'S,3S,4S) 4-[(1-phenylethyl)amino]-2,3,5,6-tetrahydro-4H-pyran-3-carboxylate hydrobromide A solution of methyl (1'S) 4-[(1-phenylethyl)amino]-5,6-dihydro-2H-pyran-3-carboxylate (1) (25 g, 95.7 mmol) in tetrahydrofuran (40 mL), methanol (60 mL), and glacial acetic acid (7.5 g) was hydrogenated in the presence of Adam's catalyst ($PtO_2$, 325 mg, 1.4 mmol) under pressure (17.5 bar) at 40° C. for 16 h. The catalyst was removed by filtration over Celite®, followed by rinsing with methanol (100 mL). The filtrate was evaporated to a low volume (approx. 60 mL) and co-evaporated with isopropyl acetate (2×200 mL). Selectivity (HPLC): 89.2% d.r. Isopropyl acetate (100 mL) was again added, followed by 30% (w/w) hydrogen bromide solution in glacial acetic acid (22.3 g, 82.7 mmol) and n-heptane (80 mL). The crystalline, white solid 3 (22.9 g, 69.4 mmol, 70%) which formed was collected by filtration and dried in vacuo for 2 h. Isomeric purity (HPLC): 98.9% d.r. IR (KBr pellet) 2945, 2860, 2790, 2480, 1750, 1580, 1465, 1235, 1095, 770, 710 cm$^{-1}$. $^1$H NMR (400 MHz, CDCl$_3$) δ 9.43 (2H, s, br.), 7.84–7.78 (2H, m), 7.50–7.40 (3H, m), 4.57 (1H, dq, J=6.1, 6.6 Hz), 4.45 (1H, m), 3.99 (1H, dd, J=4.5, 12.1 Hz), 3.88 (3H, s), 3.60 (1H, m), 3.45–3.35 (3H, m), 2.29 (1H, m), 2.12 (1H, dq, J=5.0, 12.6 Hz), 1.98 (3H, d, J=7.0 Hz). $^{13}$C NMR (100 MHz, CDCl$_3$) δ 172.6 (s), 135.9 (s), 129.8 (d), 129.7 (d, 2C), 127.9 (d, 2C), 68.0 (t), 66.6 (t), 57.1 (d), 54.1 (d), 53.5 (q), 41.2 (d), 26.7 (t), 20.5 (q). HRMS (ESI) calcd. for $C_{15}H_{21}NO_3$ (M$^+$) 263.152, found 263.152.

Compound 4: Methyl (3S,4S) 4-amino-2,3,5,6-tetrahydro-4H-pyran-3-carboxylate hydrobromide A solution of methyl (1'S,3S,4S) 4-[1-phenylethyl]amino-2,3,5,6-tetrahydro-4H-pyran-3-carboxylate hydrogen bromide salt (3) (20 g, 58.1 mmol) in methanol (110 mL) was hydrogenated in the presence 10% palladium on charcoal catalyst (50% wet, 3.7 g, 1.7 mmol) under pressure (7 bar) at 40° C. for 16 h. The catalyst was removed by filtration over Celite®, followed by rinsing with methanol (100 mL). The filtrate was evaporated to a low volume and co-evaporated with isopropyl acetate (3×100 mL). The crystalline, white solid 4 (13.3 g, 54.6 mmol, 94%) which formed was collected by filtration and dried in vacuo for 2 h. IR (KBr pellet) 3095, 2975, 2885, 1730, 1715, 1475, 1245, 1095 cm$^{-1}$. $^1$H NMR (400 MHz, d$_6$-DMSO) δ 8.17 (3H, s, br.), 4.10 (1H, dd, J=2.8, 12.1 Hz), 3.84 (1H, dt, J=3.5, 11.1 Hz), 3.67 (3H, s), 3.6 (1H, dd, J=3.0, 11.6 Hz), 3.55 (1H, dt, J=4.5, 11.1 Hz), 3.43 (1H, dt, J=2.5, 11.6 Hz), 3.3 (1H, m), 1.94 (1H, ddd, J=5.0, 11.1, 12.6 Hz), 1.75 (1H, dq, J=2.8, 12.6 Hz). $^{13}$C NMR (100 MHz, d$_6$-DMSO) δ 171.4 (s), 67.5 (t), 65.5 (t), 52.4 (q), 47.1 (t), 42.6 (d), 27.5 (q). HRMS (ESI) calcd. for $C_7H_{13}NO_3$ (M$^+$) 159.090, found 159.090.

Example 2

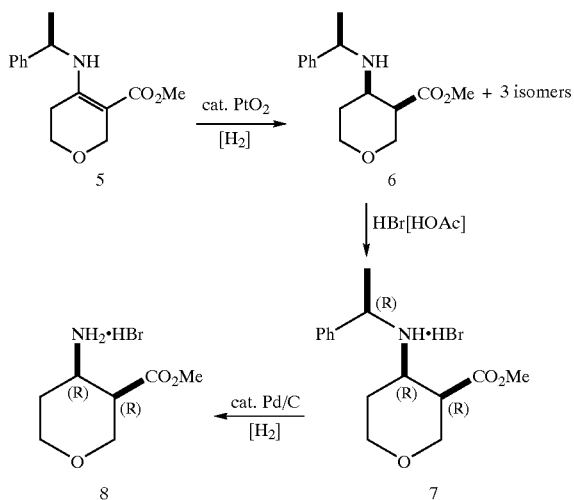

Compound 7: Methyl (1'R,3R,4R) 4-[(1-phenylethyl)amino]-2,3,5,6-tetrahydro-4H-pyran-3-carboxylate hydrobromide A solution of methyl (1'R) 4-[(1-phenylethyl)amino]-5,6-dihydro-2H-pyran-3-carboxylate (5) (2.4 kg, 9.18 mol) in tetrahydrofuran (4.8 L), methanol (7.2 L), and glacial acetic acid (0.72 kg) was hydrogenated in the presence of $PtO_2$ (31.2 g, 0.14 mol) under pressure (17.5 bar) at 40° C. for 16 h. The catalyst was removed by filtration over Celite®, followed by rinsing with methanol (2.4 L). The filtrate was evaporated to a low volume (approx. 7.0 L) and co-evaporated with isopropyl acetate (2×6.0 L). Selectivity (HPLC): 89.8 d.r. Isopropyl acetate (7.2 L) was again added, followed by 33% (w/w) hydrogen bromide solution in glacial acetic acid (2.26 kg, 9.2 mol) and n-heptane (5.8 L). The crystalline, white solid 7 (2.21 kg, 6.31 mol, 69%) which formed was collected by filtration and dried in vacuo for 2 h. Isomeric purity (HPLC): 98.3% d.r. IR (KBr pellet) 2945, 2860, 2970, 2480, 1750, 1580, 1465, 1435, 1225, 1095, 770, 710 $cm^{-1}$. $^1H$ NMR (400 MHz, $CDCl_3$) δ 9.43 (2H, s, br.), 7.84–7.78 (2H, m), 7.50–7.40 (3H, m), 4.57 (1H, dq, J=6.1, 6.6 Hz), 4.45 (1H, m), 3.99 (1H, dd, J=4.5, 12.1 Hz), 3.88 (3H, s), 3.60 (1H, m), 3.45–3.35 (3H, m), 2.29 (1H, m), 2.12 (1H, dq, J=5.0, 12.6 Hz), 1.98 (3H, d, J=7.0 Hz). $^{13}C$ NMR (100 MHz, $CDCl_3$) δ 172.6 (s), 135.9 (s), 129.8 (d), 129.7 (d, 2C), 127.9 (d, 2C), 68.0 (t), 66.6 (t), 57.1 (d), 54.1 (d), 53.5 (q), 41.2 (d), 26.7 (t), 20.5 (q). HRMS (ESI) calcd for $C_{15}H_{21}NO_3$ ($M^+$) 263.152, found 263.152.

Compound 8: Methyl (3R,4R) 4-amino-2,3,5,6-tetrahydro-4H-pyran-3-carboxylate hydrobromide A solution of methyl (1'R,3R,4R) 4-[1-phenylethyl]amino-2,3,5,6-tetrahydro-4H-pyran-3-carboxylate hydrogen bromide salt (7) (2.0 kg, 58.1 mol) in methanol (10.6 L) was hydrogenated in the presence 10% palladium on charcoal catalyst (50% wet, 380 g, 0.17 mol) under pressure (7 bar) at 40° C. for 16 h. The catalyst was removed by filtration over Celite®, followed by rinsing with methanol (6.6 L). The filtrate was evaporated to a low volume (approx. 10.0 L) and co-evaporated with isopropyl acetate (2×10.0 L). Isopropyl acetate (6.6 L) was again added and the crystalline, white solid 8 (1.37 kg, 57.1 mol, 98%) was obtained after filtration and dried in vacuo at 50° C. overnight. IR (KBr pellet) 3095, 2975, 2885, 2610, 2050, 1730, 1715, 1590, 1475, 1245, 1095 $cm^{-1}$. $^1H$ NMR (400 MHz, $d_6$-DMSO) δ 8.17 (3H, s, br.), 4.10 (1H, dd, J=2.8, 12.1 Hz), 3.84 (1H, dt, J=3.5, 11.1 Hz), 3.67 (3H, s), 3.6 (1H, dd, J=3.0, 11.6 Hz), 3.55 (1H, dt, J=4.5, 11.1 Hz), 3.43 (1H, dt, J=2.5, 11.6 Hz), 3.3 (1H, m), 1.94 (1H, ddd, J=5.0, 11.1, 12.6 Hz), 1.75 (1H, dq, J=2.8, 12.6 Hz). $^{13}C$ NMR (100 MHz, $d_6$-DMSO) δ 171.4 (s), 67.5 (t), 65.5 (t), 52.4 (q), 47.1 (t), 42.6 (d), 27.5 (q). HRMS (ESI) calcd for $C_7H_{13}NO_3$ ($M^+$) 159.090, found 159.090.

Example 3

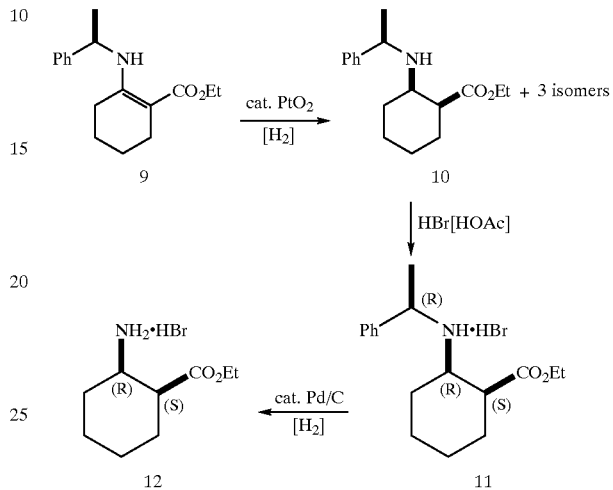

Compound 11: Ethyl (1'R,1S,2R) 2-[(1-phenylethyl)amino]-cyclohexane-1-carboxylate hydrobromide A solution of ethyl (1'R) 2-[(1-phenylethyl)amino]-1-cyclohexene-1-carboxylate (9) (35 g, 128.0 mmol) in ethanol (105 mL), and glacial acetic acid (10.0 g) was hydrogenated in the presence of $PtO_2$ (130 mg, 0.657 mmol) under pressure (17.5 bar) at 40° C. for 16 h. The catalyst was removed by filtration over Celite®, followed by rinsing with methanol (80 mL). The filtrate was evaporated to a low volume (approx. 60 mL) and co-evaporated with isopropyl acetate (2×150 mL). Selectivity (GC): 93.0% d.r. Isopropyl acetate (200 mL) was again added, followed by 30% (w/w) hydrogen bromide solution in glacial acetic acid (31.5 g, 116.8 mmol). The crystalline, white solid 11 (37.6 g, 105.5 mmol, 83%) which formed was collected by filtration and dried in vacuo for 2 h. Isomeric purity (GC): >99% d.r. IR (KBr pellet) 2940, 2795, 2505, 1730, 1580, 1460, 1185, 1030, 765, 705 $cm^{-1}$. $^1H$ NMR (400 MHz, $CDCl_3$) δ 9.40 (1H, s, br.), 9.07 (1H, s, br.), 7.84–7.79 (2H, m), 7.48–7.37 (3H, m), 4.50 (1H, dq, J=6.1, 6.6 Hz), 4.38–4.21 (2H, m), 3.43 (1H, m), 3.22 (1H, m), 2.42 (1H, m), 2.33 (1H, m), 1.95 (3H, d, J=7.0 Hz), 1.84 (1H, m), 1.68 (1H, dt, J=4.0, 12.6 Hz), 1.59 (1H, m), 1.39–1.10 (4H, m), 1.33 (3H, t, J=7.0 Hz). $^{13}C$ NMR (100 MHz, $CDCl_3$) δ 174.23 (s), 136.1 (s), 129.4 (d, 2C), 129.3 (d), 127.7 (d, 2C), 61.9 (t), 56.3 (d), 55.9 (d), 39.5 (d), 26.9 (t), 25.6 (t), 23.9 (t), 21.5 (t), 19.8 (q), 13.8 (q). HRMS (ESI) calcd for $C_{17}H_{25}NO_2$ ($M^+$) 275.189, found 275.189.

Compound 12: Ethyl (1S,2R) 2-amino-cyclohexane-1-carboxylate hydrobromide

A solution of ethyl (1'R,1S,2R) 2-[(1-phenylethyl)amino]-cyclohexane-1-carboxylate hydrogen bromide salt (11) (20 g, 56.1 mmol) in methanol (150 mL) was hydrogenated in the presence of 10% palladium on charcoal catalyst (50% wet, 3.7 g, 1.7 mmol) under pressure (7 bar) at 40° C. for 16 h. The catalyst was removed by filtration over Celite®, followed by rinsing with ethanol (80 mL). The filtrate was evaporated to an oil and co-evaporated with isopropyl acetate (3×200 mL). The crystalline, white solid 12 (12.9 g, 51.2 mmol, 91%) which formed was collected by filtration and dried in vacuo for 2 h. IR (KBr pellet) 3815, 3110, 2940, 2875, 2580, 2490, 1715, 1600, 1470, 1230, 1025 cm$^{-1}$. $^1$H NMR (400 MHz, d$_6$-DMSO) δ 7.97 (3H, s, br.), 4.18–4.04 (2H, m), 3.38 (1H, dt, J=4.0, 8.6 Hz), 2.94 (1H, dt, J=4.5, 6.1 Hz), 1.96–1.86 (1H, m), 1.83–1.55 (4H, m), 1.45–1.25 (3H, m), 1.19 (3H, t, J=7.0 Hz). $^{13}$C NMR (100 MHz, d$_6$-DMSO) δ 171.9 (s), 60.5 (t), 48.7 (d), 41.9 (d), 26.9 (t), 25.0 (t), 22.0 (t), 21.6 (t), 13.9 (q). HRMS (ESI) calcd for C$_9$H$_{17}$NO$_2$ (M$^+$) 171.126, found 171.126.

Example 4

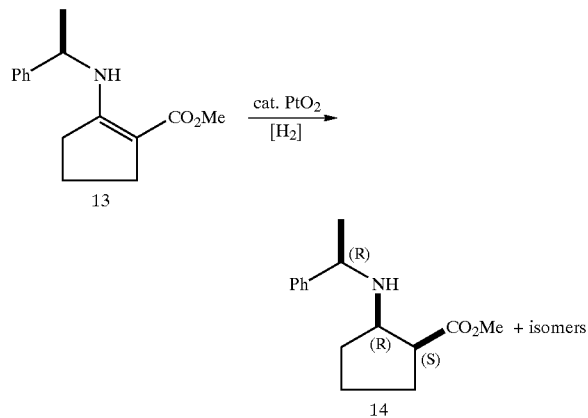

Compound 14: Methyl (1'R,1S,2R) 2-[(1-phenylethyl)amino]-cyclopentane-1-carboxylate A solution of methyl (1'R) 2-[(1-phenylethyl)amino]-1-cyclopentene-1-carboxylate (13) (20 g, 81.5 mmol) in methanol (70 mL), and glacial acetic acid (6.4 g) was hydrogenated in the presence of PtO$_2$ (460 mg, 2.0 mmol) under pressure (17.5 bar) at 40° C. for 16 h. The catalyst was removed by filtration over Celite®, followed by rinsing with methanol (80 mL). The filtrate was evaporated to an oil (22.0 g). Selectivity (HPLC): 84.6% d.r. A sample was converted to free base and analyzed. IR (film) 3345, 3085, 3060, 3025, 2960, 2870, 1730, 1600, 1450, 1195, 1170, 760, 705 cm$^{-1}$. $^1$H NMR (400 MHz, CDCl$_3$) δ 7.36–7.28 (5H, m), 7.24 (1H, s, br.), 3.81 (1H, q, J=6.5 Hz), 3.74 (3H, s), 3.10 (1H, m), 2.95 (1H, m), 2.00–1.87 (1H, m), 1.82–1.70 (3H, m), 1.60–1.49 (1H), 1.48–1.35 (1H), 1.27 (3H, d, J=6.6 Hz). $^{13}$C NMR (100 MHz, CDCl$_3$) δ 175.6 (s), 145.9 (s), 128.4 (d, 2C), 126.99d), 126.6 (d, 2C), 60.2 (d), 56.6 (d), 51.4 (q), 46.3 (d), 32.4 (t), 27.9 (t), 24.9 (t), 22.0 (q). HRMS (ESI) calcd for C$_{15}$H$_{21}$NO$_2$ (M$^+$) 247.157, found 247.157.

Example 5

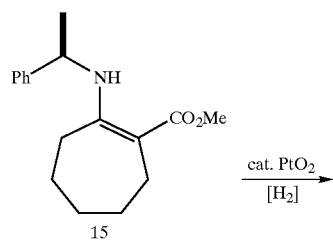

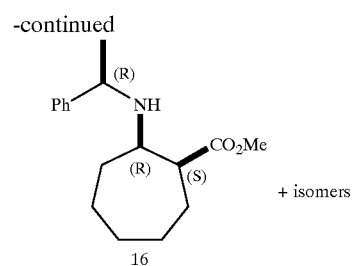

Compound 16: Methyl (1'R,1S,2R) 2-[(1-phenylethyl)amino]-cycloheptane-1-carboxylate A solution of methyl (1'R) 2-[(1-phenylethyl)amino]-1-cycloheptene-1-carboxylate (15) (10.0 g, 36.6 mmol) in methanol (100 mL), and glacial acetic acid (2.9 g) was hydrogenated in the presence of PtO$_2$ (15 mg, 0.50 mmol) under pressure (17.5 bar) at 40° C. for 16 h. The catalyst was removed by filtration over Celite®, followed by rinsing with methanol (100 mL). The filtrate was evaporated to an oil (11.9 g). Selectivity (HPLC): 96.0% d.r. A sample was converted to free base and analyzed. IR (film) 3345, 3085, 3060, 3025, 2925, 2860, 1730, 1600, 1450, 1195, 760, 700 cm$^{-1}$. $^1$H NMR (400 MHz, CDCl$_3$) δ 7.39–7.20 (5H, m), 3.86 (1H, m), 3.72 (3H, s), 2.98 (1H, m), 2.91 (1H, m), 1.91–1.60 (5H, m), 1.59–1.46 (2H, m), 1.45–1.25 (4H, m), 1.33 (3H, d, J=6.5 Hz). $^{13}$C NMR (100 MHz, CDCl$_3$) δ 175.7 (s), 145.4 (s, br.), 128.5 (d, 2C), 127.0 (d), 126.7 (d, 2C), 56.5 (d), 55.5 (d), 51.5 (q), 47.3 (d, br.), 32.9 (t, br.), 27.9 (t), 26.5 (t), 26.0 (t), 24.6 (t), 23.9 (q, br.). HRMS (ESI) calcd for C$_{17}$H$_{25}$NO$_2$ (M$^+$) 275.189, found 275.189.

Example 6

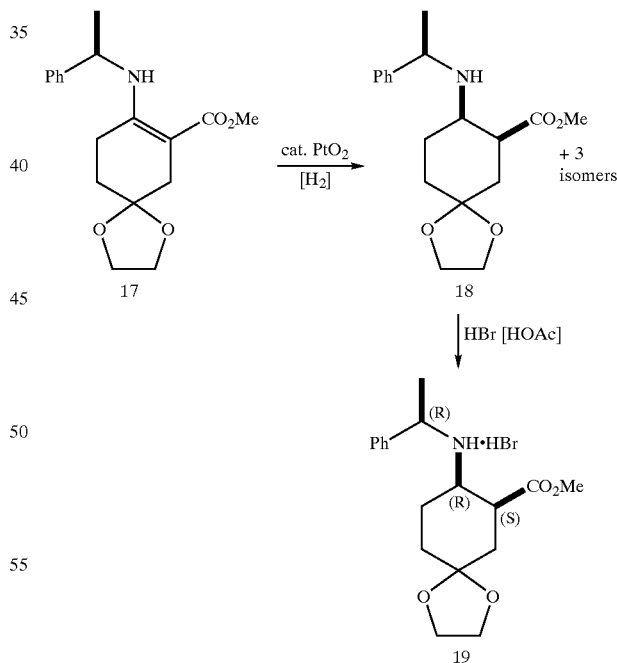

Compound 17: Methyl (1'R) 1,4-Dioxaspiro[4.5]dec-7-ene-8-[(1-phenylethyl)amino]-7-carboxylate To a solution of methyl 8-oxo-1,4-dioxaspiro[4,5]decane-7-carboxylate (500 g, 2.34 mol) and (R)-α-methylbenzylamine (283 g, 2.34 mol) in toluene (4.0 L) was charged ytterbium triflate (7.3 g, 11.7 mmol) at ambient temperature. The solution was heated to 95–100° C. for 3 h and water was azeotropically removed using a Dean-Stark trap. The reaction mixture was cooled to ambient temperature and filtered through a pad of silica gel (1" thick). The filtrate was concentrated under reduced pressure to give a yellow oil. ¹H NMR (400 MHz, CDCl₃) δ 9.45 (1H, d, J=4.2 Hz), 7.32 (2H, m), 7.26 (3H, m), 4.63 (1H, m), 3.94 (4H, m), 3.71 (3H, s), 2.57 (3H, m), 2.22 (1H, m), 1.67 (2H, m), 1.50 (3H, d, J=6.9 Hz), ¹³C NMR (100 MHz, CDCl₃) 170.8, 158.2, 145.6, 128.9, 127.2, 125.6, 107.6, 87.5, 64.7, 64.6, 52.6, 50.7, 33.9, 30.4, 25.7, 25.6. HRMS (ESI) calcd for $C_{18}H_{23}NO_4$ (M⁺) 317.163, found 317.163.

Compound 19: Methyl (1'R,7R,8S) 1,4-Dioxaspiro[4.5]decane-8-[(1-phenylethyl)amino]-7-carboxylate hydrobromide A solution of methyl (1'R) 1,4-dioxaspiro[4.5]dec-7-ene-8-[(1-phenylethyl)amino]-7-carboxylate (17) (550 g, 1.73 mol) in methanol (5.5 L) and glacial acetic acid (208 g) was hydrogenated in the presence of $PtO_2$ (31.4 g, 0.657 mmol) under pressure (17.5 bar) at 20–22° C. for 16 h. The catalyst was removed by filtration over Celite®, followed by rinsing with methanol (1.0 L). The filtrate was evaporated to a viscous oil. Selectivity (¹H NMR): 90% d.r. The oil was taken into isopropyl acetate (500 mL) and was filtered through a pad of silica gel (150 g). To the filtrate was added 30% hydrogen bromide in acetic acid (126 g). Once a solid was observed, n-heptane (2.0 L) was added and the mixture was cooled to 0° C. and stirred for 2 h. The crystalline, white solid 19 (416 g, 1.04 mol, 60%) was collected by filtration and dried in vacuo for 2 h. A second crop was taken by distilling the liquors to one fifth volume adding n-heptane (1.0 L) and stirring over night (90.0 g, 0.225 mol, 13%). Isomeric purity (¹H NMR): >95% d.r. (single isomer observed). IR (KBr pellet) 3440, 2950, 2790, 2485, 1740, 1580, 1455, 1170, 1085, 770, 705 cm⁻¹. ¹H NMR (400 MHz, CDCl₃) δ 9.20 (2H, Br s), 7.83 (2H, d, J=7.1 Hz), 7.47–7.38 (3H, m), 4.54–4.49 (1H, q, J=7.1 Hz) 4.00–3.74 (7H, m), 3.58–3.52 (1H, m), 3.40–3.30 (1H, m), 2.49–2.36 (2H, m), 2.19–2.00 (1H, m), 1.96 (3H, d, J=7.1 Hz), 1.89–1.78 (1H, m), 1.68–1.56 (2H, m). ¹³C NMR (100 MHz, CDCl₃) δ 174.4, 136.1, 129.8, 128.1, 106.3, 64.9, 64.3, 57.6, 54.8, 52.7, 38.9, 34.4, 33.2, 23.6, 20.3. HRMS (ESI) calcd for $C_{18}H_{25}NO_4$ (M⁺) 319.178, found 319.178.

Example 7

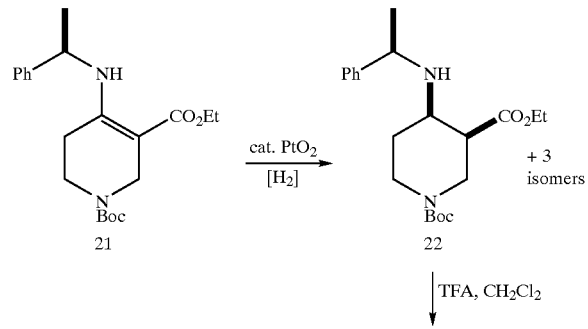

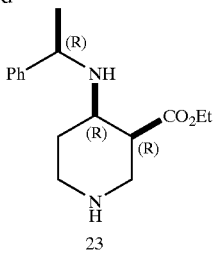

Compound 23: Ethyl (1'R,3R,4R) 4-[(1-phenylethyl)amino]-piperidine-3-carboxylate A solution of ethyl (1'R) 1-[(1,1-dimethyl)ethyl]-4-[(1-phenylethyl)amino]-5,6-dihydro-2H-pyridinecarboxylate (21) (5.3 g, 914.2 mmol) in ethanol (80 mL) and glacial acetic acid (1.7 g) was hydrogenated in the presence of $PtO_2$ (80 mg, 0.35 mmol) under pressure (17.5 bar) at rt for 30 h. The catalyst was removed by filtration over Celite®, followed by rinsing with ethanol (100 mL). The filtrate was evaporated to an oil, taken into $CH_2Cl_2$ and washed twice with 10% NaOH, dried over sodium sulfate and evaporated to an oil (4.81 g, 12.8 mmol, 90.3%). The crude product was not characterized due to a complex NMR spectrum as a result of the presence of rotamers. The N-Boc protected amino ester (2.03 g, 5.39 mmol) was dissolved in $CH_2Cl_2$ (20 mL) and TFA (1 mL) was added. The mixture was stirred at room temperature for 16 h. The mixture was extracted with 10% aqueous NaOH solution, dried over sodium sulfate and evaporated to give an oil. Selectivity (¹H NMR): 83% d.r. ¹H NMR (400 MHz, CDCl₃) δ 7.37–7.15 (5H, m); 4.18 (1.7H, q, J=7.6 Hz [4.09 (0.3H, q, J=7.1 Hz)]; 3.76 (1H, q, J=6.6 Hz) 3.07–2.98 (1H, m); 2.94 (1H, dd, J=4.0, 12.6); 2.75 (1H, dd, J=4.5, 12.1); 2.61 (1H, dt, J=4.0, 10.6); 2.51 (2H, dt, J=3.1, 12.7); 1.95–1.75 (3H, m); 1.63–1.53 (1H, m); 1.40–1.20 (6H, m).

Numerous modifications and variations of the present invention are possible in light of the above teachings. It is therefore to be understood that within the scope of the appended claims, the invention may be practiced otherwise than as specifically described herein.

What is claimed is:

1. A process of forming a compound of formula II, comprising:

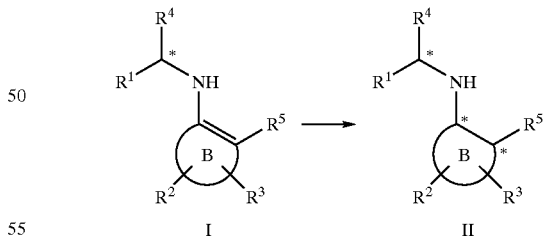

(a) contacting a compound of formula I with sub-stoichiometric amounts of a platinum catalyst in the presence of a solvent under hydrogen pressure and super-stoichiometric amounts of an acid; wherein:
the platinum catalyst is platinum on charcoal (Pt/C) or Adam's catalyst (platinum(IV)-dioxide, $PtO_2$);
the solvent is a protic solvent or a mixture of protic and aprotic solvents;
ring B is a 4–7 membered non-aromatic carbocyclic or heterocyclic ring consisting of: carbon atoms, 0–3 carbonyl groups, 0–3 double bonds, and 0–2 ring heteroatoms selected from O, N, $NR^6$, and $S(O)_p$, provided that ring B contains other than a S—S, O—O, or S—O bond;

$R^1$ is Q, —$C_{1-6}$ alkylene-Q, —$C_{2-6}$ alkenylene-Q, or —$C_{2-6}$ alkynylene-Q;

$R^2$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$-Q, —$(CR^aR^{a1})_rNR^a(CR^aR^{a1})_s$-Q, —$(CR^aR^{a1})_rC(O)(CR^aR^{a1})_s$-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rS(O)_p(CR^aR^{a1})_s$-Q, or —$(CR^aR^{a1})_rSO_2NR^a(CR^aR^{a1})_s$-Q;

Q is, independently at each occurrence, H, a $C_{3-6}$ carbocycle substituted with 0–3 $R^d$, or a 5–10 membered heterocycle consisting of: carbon atoms and 1–4 heteroatoms selected from the group consisting of N, O, and $S(O)_p$, and substituted with 0–3 $R^d$;

$R^3$ is H, Cl, F, $C_{1-6}$ alkyl, $C_{2-6}$ alkenyl, $C_{2-6}$ alkynyl, —$(CH)_r$-phenyl substituted with 0–3 $R^d$, or —$(CH)_r$-5–6 membered heterocycle consisting of: carbon atoms and 1–4 heteroatoms selected from the group consisting of N, O, and $S(O)_p$, and substituted with 0–3 $R^d$;

alternatively, when $R^2$ and $R^3$ are attached to the same carbon atom, they form a 3–8 membered carbocyclic or heterocyclic spiro ring C substituted with 0–2 $R^c$ and consisting of carbon atoms, 0–4 heteroatoms selected from O, N, and $S(O)_p$, and 0–2 double bonds, provided that ring C contains other than a S—S, O—O, or S—O bond;

alternatively, when $R^2$ and $R^3$ are attached to adjacent carbon atoms, together with the carbon atoms to which they are attached they form a 5–7 membered carbocyclic or heterocyclic ring D substituted with 0–2 $R^c$ and consisting of carbon atoms, 0–2 heteroatoms selected from the group consisting of N, O, and $S(O)_p$, and 0–3 double bonds;

$R^4$ is H, $C_{1-6}$ alkyl substituted with 0–1 $R^b$, $C_{2-6}$ alkenyl substituted with 0–1 $R^b$, or $C_{2-6}$ alkynyl substituted with 0–1 $R^b$;

$R^5$ is —$CH_2OR^a$ or —$C(O)OR^a$;

$R^6$ is Q, —$C_{1-6}$ alkylene-Q, —$C_{2-6}$ alkenylene-Q, —$C_{2-6}$ alkynylene-Q, —$(CR^aR^{a1})_rC(O)(CR^aR^{a1})_s$-Q, —$(CR^aR^{a1})_rC(O)$—$C_{2-6}$ alkenylene-Q, —$(CR^aR^{a1})_rC(O)O(CR^aR^{a1})_s$-Q, —$(CR^aR^{a1})_rC(O)NR^aR^{a1}$, —$(CR^aR^{a1})_rC(O)NR^a(CR^aR^{a1})_s$-Q, —$(CR^aR^{a1})_rS(O)_p(CR^aR^{a1})_s$-Q, or —$(CR^aR^{a1})_rSO_2NR^a(CR^aR^{a1})_s$-Q;

$R^a$ is, independently at each occurrence, H, $C_{1-6}$ alkyl, phenyl, or benzyl;

$R^{a1}$ is, independently at each occurrence, H or $C_{1-6}$ alkyl;

$R^{a2}$ is, independently at each occurrence, $C_{1-6}$ alkyl, phenyl, or benzyl;

$R^b$ is, independently at each occurrence, $C_{1-6}$ alkyl substituted with 0–1 $R^c$, —$OR^a$, —$SR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a2}$, —$NR^aS(O)_2NR^aR^{a1}$, —$OS(O)_2NR^aR^{a1}$, —$S(O)_pR^{a2}$, $CF_3$, —$CF_2CF_3$, —$CHF_2$, —$CH_2F$, or phenyl;

$R^c$ is, independently at each occurrence, H, $C_{1-4}$ alkyl, —$OR^a$, Cl, F, Br, I, =O, $CF_3$, CN, $NO_2$, —$C(O)R^a$, —$C(O)OR^a$, —$C(O)NR^aR^a$, or —$S(O)_pR^a$;

$R^d$ is, independently at each occurrence, $C_{1-6}$ alkyl, —$OR^a$, Cl, F, Br, I, =O, CN, $NO_2$, —$NR^aR^{a1}$, —$C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a2}$, —$NR^aS(O)_2NR^aR^{a1}$, —$OS(O)_2NR^aR^{a1}$, —$S(O)_pR^{a2}$, $CF_3$, —$CF_2CF_3$, $C_{3-10}$ carbocycle, or a 5–6 membered heterocycle consisting of: carbon atoms and 1–4 heteroatoms selected from the group consisting of N, O, and $S(O)_p$;

p, at each occurrence, is selected from 0, 1, and 2;

r, at each occurrence, is selected from 0, 1, 2, 3, and 4; and s, at each occurrence, is selected from 0, 1, 2, 3, and 4.

2. A process according to claim 1, to form a compound of formula II, wherein:

ring B is:

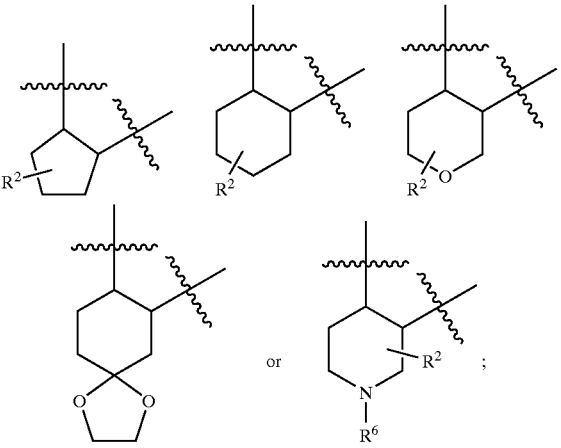

$R^1$ is phenyl substituted with 0–3 $R^d$;

$R^2$ is Q, —$C_{1-6}$ alkylene-Q, —$C_{2-4}$ alkenylene-Q, —$C_{2-4}$ alkynylene-Q, —$C(O)(CR^aR^{a1})_s$-Q, —$C(O)O(CR^aR^{a1})_s$-Q, —$C(O)NR^aR^{a1}$, —$C(O)NR^a(CR^aR^{a1})_s$-Q, —$S(O)_p(CR^aR^{a1})_s$-Q, or —$SO_2NR^a(CR^aR^{a1})_s$-Q;

Q is, independently at each occurrence, H, cyclopropyl, cyclobutyl, cyclopentyl, cyclohexyl, tetrahydro-2H-pyran-4-yl, or phenyl substituted with 0–2 $R^d$;

$R^4$ is $C_{1-4}$ alkyl;

$R^5$ is —$CH_2OR^a$ or —$C(O)OR^a$;

$R^6$ is Q, —$C_{1-6}$ alkylene-Q, —$C_{2-4}$ alkenylene-Q, —$C_{2-4}$ alkynylene-Q, —$C(O)(CR^aR^{a1})_s$-Q, —$C(O)O(CR^aR^{a1})_s$-Q, —$C(O)NR^aR^{a1}$, —$C(O)NR^a(CR^aR^{a1})_s$-Q, —$S(O)_p(CR^aR^{a1})_s$-Q, or —$SO_2NR^a(CR^aR^{a1})_s$-Q; and $R^d$ is, independently at each occurrence, $C_{1-6}$ alkyl, —$OR^a$, Cl, F, Br, =O, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a2}$, —$S(O)_pR^{a2}$, $CF_3$ or phenyl.

3. A process according to claim 2, to form a compound of formula II, wherein:

ring B is:

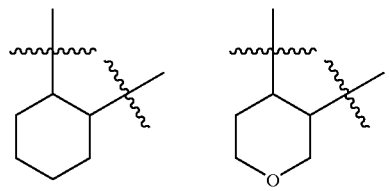

-continued

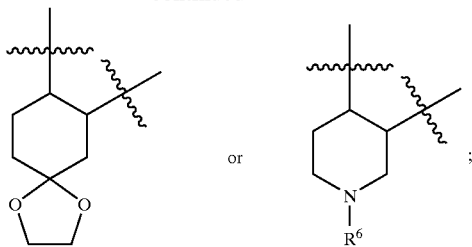

$R^1$ is phenyl;
$R^4$ is $C_{1-4}$ alkyl;
$R^5$ is —C(O)OR$^a$;
$R^6$ is H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and
$R^a$ is $C_{1-4}$ alkyl.

4. A process according to claim 1, further comprising:
(b) contacting the product from (a) with a hydrogen bromide solution in an acid to yield compound III;

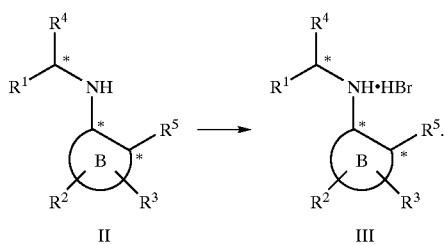

5. A process according to claim 4, further comprising:
(c) contacting the product from (b) with palladium on charcoal catalyst (Pd/C) in the presence of a solvent under hydrogen pressure to yield compound IV; wherein the solvent is a protic solvent or a mixture of protic and aprotic solvents;

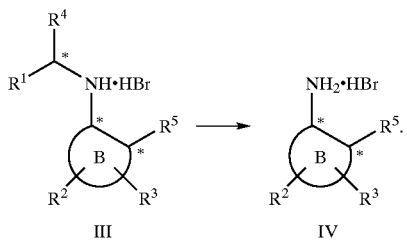

6. A process according to claim 1, wherein in (a):
the protic solvent is selected from: methanol, ethanol, propanol, 2-butanol, water, ethylene glycol, propylene glycol, and butylene glycol; and
the aprotic solvent is selected from: tetrahydrofuran, dibutyl ether, 1,2-dimethoxyethane, dimethoxymethane, and diethoxymethane.

7. A process according to claim 6, wherein in (a):
the protic solvent is selected from: methanol, ethanol, propanol, and 2-butanol; and
the aprotic solvent is selected from: tetrahydrofuran and dimethoxymethane.

8. A process according to claim 7, wherein in (a):
the protic solvent is methanol; and
the aprotic solvent is tetrahydrofuran.

9. A process according to claim 1, wherein in (a):
the hydrogen pressure is 10 to 400 psig.

10. A process according to claim 9, wherein in (a):
the hydrogen pressure is 100 to 300 psig.

11. A process according to claim 10, wherein in (a):
the hydrogen pressure is 250 psig.

12. A process according to claim 1, wherein in (a):
the acid is selected from: formic acid, acetic acid, chloroacetic acid, dichloroacetic acid, trichloroacetic acid, trifluoroacetic acid, propionic acid, isobutyric acid, hydrochloric acid, and sulfuric acid.

13. A process according to claim 12, wherein in (a):
the acid is acetic acid.

14. A process according to claim 4, wherein in (b):
the acid is acetic acid or formic acid.

15. A process according to claim 14, wherein in (b):
the acid is acetic acid.

16. A process according to claim 5, wherein in (c):
the protic solvent is selected from: methanol, ethanol, propanol, 2-butanol, water, ethylene glycol, propylene glycol, and butylene glycol; and
the aprotic solvent is selected from: tetrahydrofuran, dibutyl ether, 1,2-dimethoxyethane, dimethoxymethane, and diethoxymethane.

17. A process according to claim 16, wherein in (c):
the protic solvent is selected from: methanol, ethanol, propanol, and 2-butanol; and
the aprotic solvent is selected from: tetrahydrofuran and dimethoxymethane.

18. A process according to claim 17, wherein in (c):
the protic solvent is methanol; and
the aprotic solvent is tetrahydrofuran.

19. A process according to claim 5, wherein in (c):
the hydrogen pressure is 20 to 300 psig.

20. A process according to claim 19, wherein in (c):
the hydrogen pressure is 50 to 150 psig.

21. A process according to claim 20, wherein in (c):
the hydrogen pressure is 100 psig.

22. A process according to claim 1, wherein:
the diastereomeric ratio of the product of (a), Compound of formula II, is at least 60%.

23. A process according to claim 22, wherein:
the diastereomeric ratio of the product of (a), Compound of formula II, is at least 80%.

24. A process according to claim 5, wherein:
the diastereomeric ratio of the product of (c), Compound of formula IV, is at least 60%; and, the enantiomeric ratio of the product of (c), Compound of formula IV, is at least 60%.

25. A process according to claim 24, wherein:
the diastereomeric ratio of the product of (c), Compound of formula IV, is at least 80%; and
the enantiomeric ratio of the product of (c), Compound of formula IV, is at least 80%.

* * * * *